United States Patent [19]

Houser et al.

[11] Patent Number: 5,573,522
[45] Date of Patent: Nov. 12, 1996

[54] SPRING ASSEMBLY FOR CATHETER

[75] Inventors: Russell A. Houser, Livermore; Russell B. Thompson, Los Altos, both of Calif.

[73] Assignee: EP Technologies, Inc., Sunnyvale, Calif.

[21] Appl. No.: 528,254

[22] Filed: Sep. 14, 1995

Related U.S. Application Data

[63] Continuation of Ser. No. 320,322, Oct. 11, 1994, abandoned.

[51] Int. Cl.$^6$ ................................................. A61M 25/00
[52] U.S. Cl. ......................... 604/282; 604/280; 604/264
[58] Field of Search .................................. 604/280–282, 604/264, 164–170, 96–103

[56]  References Cited

U.S. PATENT DOCUMENTS

| | | |
|---|---|---|
| 3,749,086 | 7/1973 | Kline et al. . |
| 3,757,768 | 9/1973 | Kline . |
| 4,020,829 | 5/1977 | Willson et al. . |
| 4,033,331 | 7/1977 | Guss et al. . |
| 4,161,952 | 7/1979 | Kinney et al. . |
| 4,454,888 | 6/1984 | Gold . |
| 4,456,017 | 6/1984 | Miles . |
| 4,516,972 | 5/1985 | Samson . |
| 4,545,390 | 10/1985 | Leary . |
| 4,554,929 | 11/1985 | Samson et al. . |
| 4,586,923 | 5/1986 | Gould et al. . |
| 4,649,922 | 3/1987 | Wiktor . |
| 4,659,328 | 4/1987 | Potter et al. . |
| 4,676,249 | 6/1987 | Arenas et al. . |
| 4,677,990 | 7/1987 | Neubauer . |
| 4,886,067 | 12/1989 | Palermo . |
| 4,909,787 | 3/1990 | Danforth . |
| 5,055,101 | 10/1991 | McCoy . |
| 5,069,674 | 12/1991 | Fearnot et al. . |
| 5,176,660 | 1/1993 | Truckai . |
| 5,211,636 | 5/1993 | Mische . |
| 5,226,888 | 7/1993 | Arney . |
| 5,313,967 | 5/1994 | Lieber et al. . |

Primary Examiner—Randall L. Green
Assistant Examiner—Perry E. Van Over
Attorney, Agent, or Firm—Ryan, Maki, Mann & Hohenfeldt, S.C.

[57]  ABSTRACT

A catheter having a proximal portion and a distal portion terminating in a distal tip, is provided with a spring assembly contained within its distal tip portion for providing a bias against side to side deflection of said distal tip. The assembly preferably includes a central wire having a first diameter, which central wire extends from the proximal portion of the catheter to the distal portion, and a plurality of wires secured to the central wire adjacent the distal end thereof. Each of the wires is stranded together, preferably twisted helically, around the central wire and preferably has a second diameter substantially smaller than the first diameter. Alternatively, the stranded wires can be attached along and parallel to the larger diameter wire, and the latter wire is of a substantially greater length than the stranded wires.

5 Claims, 2 Drawing Sheets

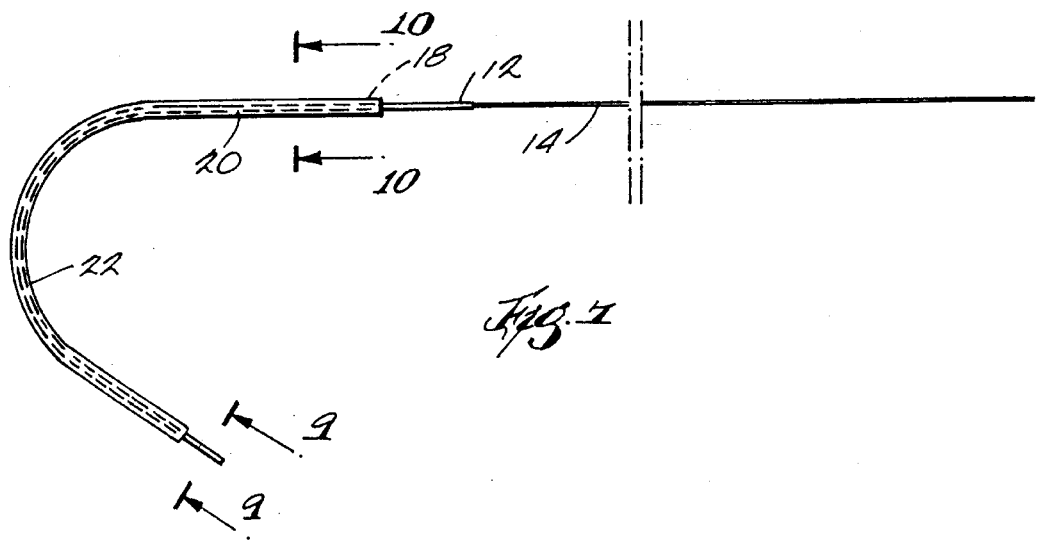
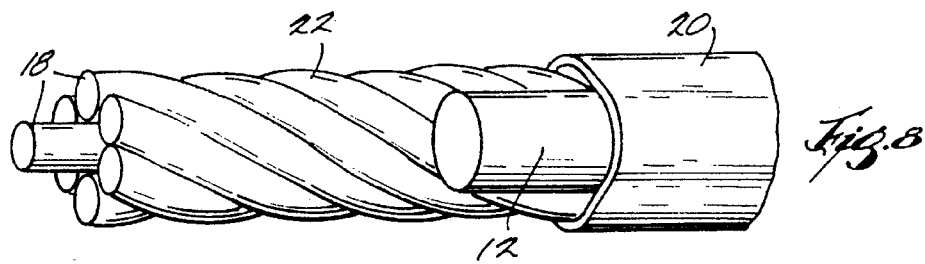
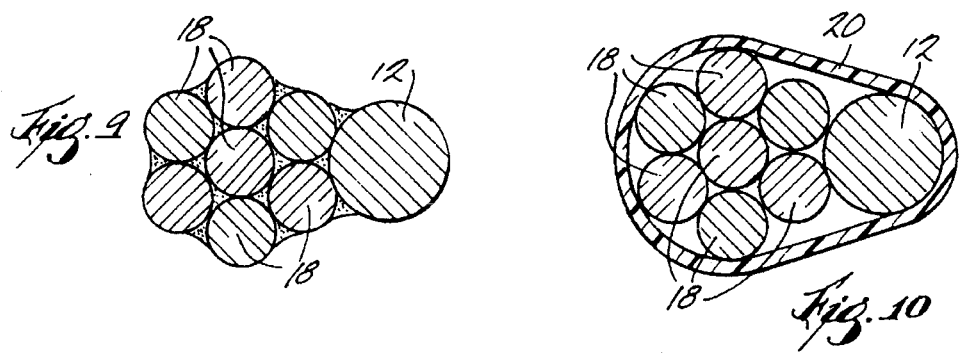
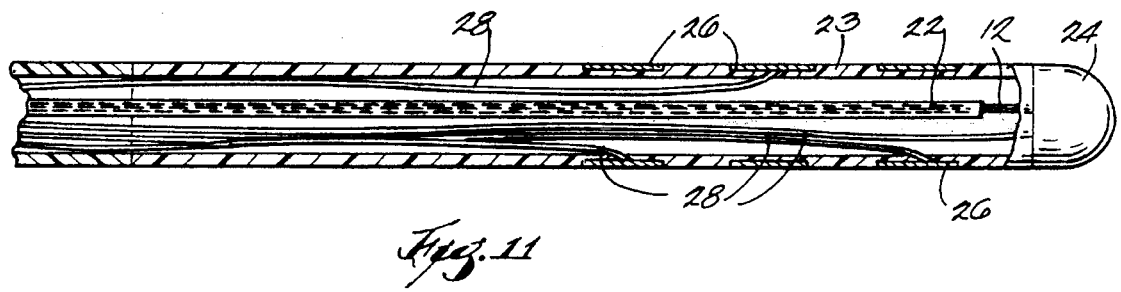

SPRING ASSEMBLY FOR CATHETER

This is a continuation of application(s) Ser. No. 08/320,322 filed on Oct. 11, 1994 now abandoned.

BACKGROUND OF THE INVENTION

This invention relates to catheters for in vivo insertion into a living body and particularly those used for insertion into the cardiovascular system for cardiac monitoring and therapy.

Many catheters require an atraumatic, but constant, tissue contact, for example, electro-physiology catheters. However, existing catheters have either been soft and atraumatic but sacrifice the ability to provide constant tissue contact, or, on the other hand, provide good tissue contact but are rigid and, thus, increase the risk of tissue perforations. A need has, thus, existed for catheters having the ability to provide a firm constant contact with tissues such as cardiac tissues without risk of perforation of the tissue.

SUMMARY OF THE INVENTION

It is a primary object of the present invention to provide a catheter having a novel interior spring configuration that enables the distal tip section of a catheter to provide a firm but atraumatic contact with tissue. In accordance with a related aspect of the invention, the exceptional tissue contact provided by the catheters of the present invention provides for improved pacing, sensing of electrical signals and recording performance, for example, within the living heart without compromising safety. In accordance with a further related aspect, the invention provides the dual benefit of maintaining a predictable distal tip tissue contact while still achieving a deflectable atraumatic distal tip that permits insertion of the catheter without injury to the patient.

In accordance with a further aspect of the invention, a cable spring assembly for a catheter distal tip is provided from a number of individual small gauge wires stranded together. In accordance with a further related aspect, the stranded wires can be preferably used in connection with a single wire of larger diameter. In accordance with yet another aspect of the invention, the various wires used in the spring subassembly may be provided from different metals such as stainless steel and copper to provide springs having preselected stiffness, elasticity and recovery rates. In accordance with yet another aspect of the invention, the spring assembly is preferably jacketed by means of a polymeric sheath.

In accordance with a still further aspect of the invention, the spring assembly can be provided from wires that have a dual purpose. For example, one or more wires can be used as a distal tip anchor (safety) wire and other wires can be used as electrode signal wires.

Briefly, in accordance with one preferred embodiment of the invention, a catheter having a proximal portion and a distal portion terminating in a distal tip, is provided with a spring assembly contained within its distal tip portion for providing a bias against side-to-side deflection of said distal tip. The assembly preferably includes a central wire having a first diameter, which central wire extends from the proximal portion of the catheter to the distal portion, and a plurality of wires secured to the central wire adjacent the distal end thereof. Each of the wires is stranded together, preferably twisted helically, around the central wire and preferably has a second diameter substantially smaller than the first diameter. Alternatively, the stranded wires can be attached along and parallel to the larger diameter wire, and the latter wire is of a substantially greater length than the stranded wires.

BRIEF DESCRIPTION OF THE DRAWINGS

The foregoing and other objects and advantages of the invention will be more fully apparent from the following detailed description and accompanying drawings wherein:

FIG. 7 is a fragmentary side view of a spring subassembly in accordance with a further embodiment of the invention;

FIG. 8 is a fragmentary isometric view of a section of the distal tip of the subassembly shown in FIG. 7;

FIG. 9 is a sectional view taken along line 9—9 of FIG. 7;

FIG. 10 is a sectional view taken along line 10—10 of FIG. 7; and

FIG. 11 is a central sectional view of the catheter of FIG. 7.

DETAILED DESCRIPTION OF PREFERRED EMBODIMENTS

Figure 1:
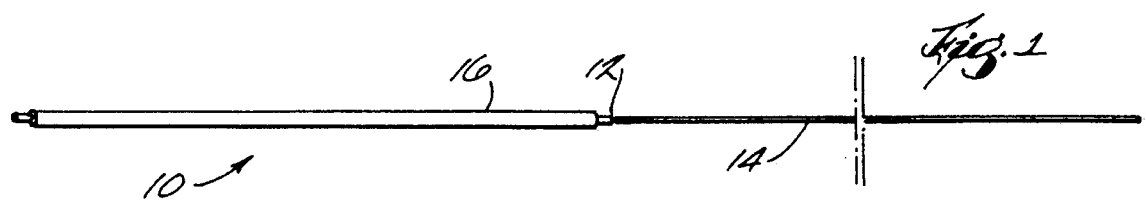
FIG. 1 is a fragmentary isometric view of a preferred embodiment of a spring assembly in accordance with the invention.
Figure 2:
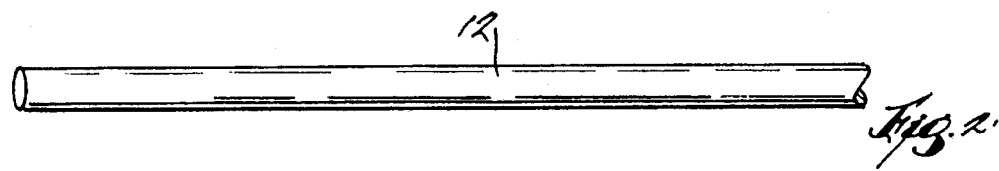
FIG. 2 is a fragmentary isometric view of a component of the spring assembly of the present invention.
Figure 3:
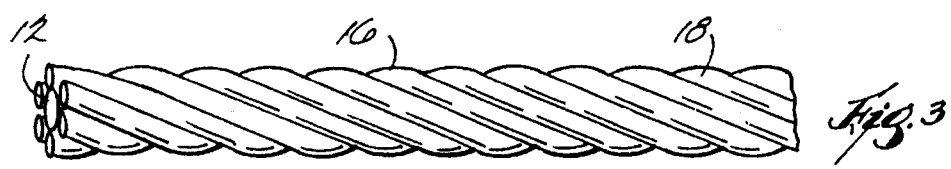
FIG. 3 is a fragmentary isometric view of the component of FIG. 2 with further strands of spring material in accordance with the invention.
Figure 4:
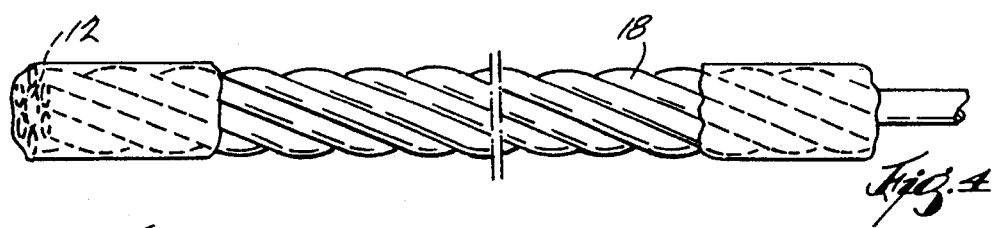
FIG. 4 is a fragmentary isometric view with parts broken away of a section of the distal tip spring assembly shown in FIG. 1.
Figure 5:
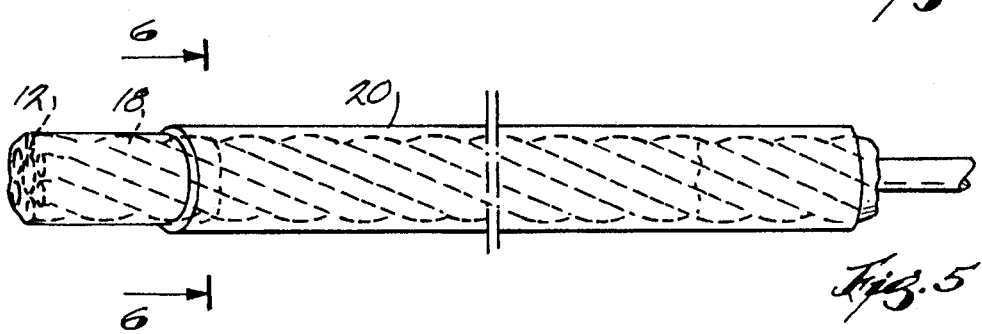
FIG. 5 is a fragmentary isometric view of the subassembly shown in FIG. 4 with a polymeric jacket placed thereon.
Figure 6:
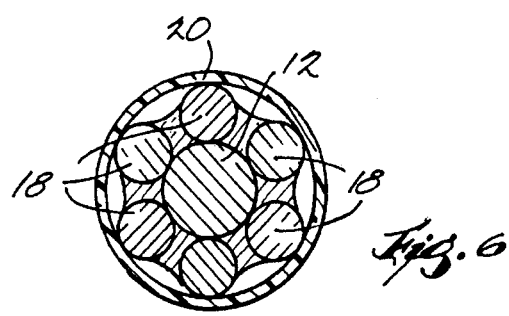
FIG. 6 is a sectional view taken along line 6—6 of FIG. 5.

Referring more particularly to the drawings, there is seen in FIG. 1 a spring assembly 10 in accordance with the invention. In accordance with the illustrated embodiment, assembly 10 includes a relatively larger diameter wire formed, for example, from stainless steel 12. Wire 14 would generally extend from the proximal end of the catheter to its distal end and may be, for example, either an anchor wire or signal wire attached at its distal end to a distal end electrode on the catheter. A stranded spring assembly 16 is preferably wound around larger diameter wire 12. The individual strands 18 of stranded portion 16 may be additional smaller diameter stainless steel wires or alternatively could be copper wires in the event that less spring force is desired. When more spring force is desired a more rigid wire such as Elgiloy (T.M.), a cobalt-chromium-nickel alloy is used. The cross-section of individual strands 18 could be circular, square or rectangular. It is preferred that the spring subassembly be encased in a layer of plastic material 20 which may be PTFE or another appropriate plastic material.

An alternative embodiment of the invention is shown in FIGS. 7–11 wherein an alternative subassembly 22 is provided. As best seen in FIGS. 8–10, the spring subassembly 22 includes a larger diameter wire 12 secured adjacent and parallel to a helically stranded bundle of smaller diameter individual wires 18. As seen in FIG. 10, a layer of plastic material 20 can be used to encase the subassembly.

As seen in FIG. 7, the spring subassembly 22 is provided with a curved portion as illustrated. This curved portion can be formed by simultaneously bending and heating the wire subassembly. Upon cooling the subassembly retains a permanent set into the illustrated curve configuration.

A typical installation of spring subassembly 22 into a distal end of a catheter 23 is seen in FIG. 11. Catheter distal end 23 includes an end electrode 24 secured to the distal extremity thereof. A plurality of ring electrodes 26 can be secured concentrically around the body of the catheter 23 in the distal end portion for sensing purposes. For example, each ring electrode 26 can be attached to a separate electrical lead wire 28. The lead wires and spring subassembly 22 are all located within the lumen of the catheter body 23 as illustrated. Wire 12 can be utilized as either an anchor wire for tip electrode 24 or a signal wire or both.

While preferred embodiments of the invention have been shown for purposes of illustration, it will be understood by those skilled in the art that numerous modifications can be made falling within the spirit of the invention and the scope of the appended claims, including equivalents thereof.

What is claimed is:

1. A catheter having a proximal portion and a distal portion terminating in a distal tip, and at least one interior lumen extending axially therethrough, a spring assembly contained within said lumen in said distal portion, said spring assembly providing a bias for return of said distal portion, if deflected, to a preselected orientation, said assembly comprising a plurality of stranded elongated wires positioned axially within said distal portion.

2. A catheter according to claim 1 wherein said wires comprise a metal.

3. A catheter according to claim 2 wherein said wires comprise stainless steel.

4. A catheter having a proximal portion and a distal portion terminating in a distal tip, a spring assembly contained within said distal tip portion for providing a bias against side to side deflection of said distal tip, said assembly comprising a central wire having a first diameter, said central wire extending from said proximal portion of said catheter to said distal portion, and a plurality of wires secured to said central wire adjacent the distal end thereof, each of said wires being twisted helically around said central wire and having a second diameter substantially smaller than said first diameter.

5. A catheter according to claim 4 wherein said spring assembly is curved into a preselected radius of curvature.

* * * * *